US006310037B1

(12) United States Patent
Takemoto et al.

(10) Patent No.: US 6,310,037 B1
(45) Date of Patent: Oct. 30, 2001

(54) METHOD OF CONTROLLING PROTOZOAN INFECTIONS USING SYRINGOMYCIN-FAMILY LIPODEPSIPEPTIDES

(75) Inventors: Jon Y. Takemoto, North Logan, UT (US); John R. Forney, Wrair Washington, DC (US); Mark C. Healey, Utah State University; Shiguang Yang, Logan, both of UT (US); Karl A. Werbovetz, Montgomery Village, MD (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 09/299,266

(22) Filed: Apr. 26, 1999

(51) Int. Cl.[7] .............................. A01N 37/18; A61K 38/00
(52) U.S. Cl. .................................. 514/2; 514/11; 514/15; 435/253.3; 435/252.34; 530/317; 530/328; 530/300
(58) Field of Search .................... 514/11, 15; 435/253.3, 435/252.34; 530/317, 328, 300

(56) References Cited

U.S. PATENT DOCUMENTS

| 5,576,298 | 11/1996 | Strobel et al. | 514/15 |
|---|---|---|---|
| 5,750,496 | 5/1998 | Forney et al. | 530/378 |
| 5,830,855 | 11/1998 | Takemoto | 514/11 |
| 5,837,685 | 11/1998 | Strobel et al. | 514/15 |

OTHER PUBLICATIONS

Bonnin et al., "Characterization and immunolocalization of an oocyst wall antigen of *Cryptosporidium parvum* (Protozoa: Apicomplexa)", *Parasitology*, 103, pp. 171–177, 1991.

Gellin et al., "Coccidian Infections In Aids", *Medical Management Of Aids Patients,* vol. 76, No. 1, pp. 205, 216–222, Jan. 1992.

Levine, Norman D., "The Biology of the Coccidia", Edited by Peter L. Long, University Park Press Baltimore, pp. 1–33, 1982.

O'Donoghue, Peter J., "Cryptosporidium and Cryptosporidiosis in Man and Animals", *International Journal for Parasitology,* vol. 25, No. 2, pp. 139, 154–155, 165–169, 1995.

Petersen, C., "Cellular Biology of *Cryptosporidium parvum*", *Parasitology Today,* vol. 9, No. 3, pp. 87–91, 1993.

Phillips et al., "Cryptosporidium, chronic diarrhoea and the proximal small intestinal mucosa", *Gut,* 4 pages, Aug. 1992.

Egan et al., Infection and Immunity (Mar. 2000) 68(3): 1418–1427.*

Sorensen et al, Antimicrobial Agents and Chemotherapy, (1996) 40(12): 2710–13.*

\* cited by examiner

*Primary Examiner*—Christoper S. F. Low
*Assistant Examiner*—Stephen Tu
(74) *Attorney, Agent, or Firm*—TraskBritt

(57) ABSTRACT

A method for controlling infections caused by protozoans, such as *Cryptosporidium parvum, Plasmodium falciparum,* and *Leishmania donovani.* The method comprises using syringomycin-family lipodepsipeptides, preferably syringomycins such as syringomycin E, to control or prevent infections caused by protozoans. The method is directed to therapeutic treatment of mammals, such as humans, exposed to protozoans, and additionally as a prophylactic treatment in immunocompromised subjects at high risk for contracting protozoan infections.

16 Claims, 2 Drawing Sheets

METHOD OF CONTROLLING PROTOZOAN INFECTIONS USING SYRINGOMYCIN-FAMILY LIPODEPSIPEPTIDES

TECHNICAL FIELD

The present invention relates to anti-protozoal therapy generally and, more specifically, to a method of controlling infections caused by protozoans using Syringomycin-family lipodepsipeptides.

BACKGROUND

Parasitic infections are a major worldwide health problem, with a global prevalence of human parasitic infection exceeding 50% and increasing. Parasites are found in four divisions of the animal kingdom, one of which is the Protozoa which include *C. parvum, L. donovani,* and *P. falciparum.*

*C. parvum* is a coccidian protozoan that infects the epithelial cells lining the digestive and respiratory tracts of mammals. The protozoan preferentially invades the epithelial cells lining the microvilli lining the small intestine, but all sites of the gastrointestinal tract (including the esophagus, stomach, colon, common bile duct, gall bladder, liver, rectum, and pancreatic duct) can be involved. The most common clinical manifestations of the resulting infection, commonly called cryptosporidiosis, are characterized by voluminous watery diarrhea, cramping abdominal pain, and weight loss. Nausea, vomiting, fatigue, headache, and myalgia may also be present. In immunocompetent individuals, the infection causes a generally self-limited diarrhea and results in spontaneous eradication of the parasite from the intestinal mucosa and a protective acquired immunity. Severe consequences of cryptosporidiosis, however, can occur in hosts with immature or deficient immune systems. These include young children (usually under five years old), patients undergoing immunosuppressive drug therapy, geriatric hosts having decreased immune responsiveness, and patients with congenital or acquired immunodeficiencies (e.g., Human Immunodeficiency Virus ("HIV") infected and Acquired Immunodeficiency Syndrome ("AIDS") patients). These individuals frequently develop a profuse, protracted diarrheal illness which progresses to a chronic infection of the intestinal epithelium and, potentially, cryptosporidial dissemination into the alveolar and tracheal epithelium.

At least five species of Plasmodium infect humans. Of these, *P. falciparum* is responsible for the most serious form of malaria. The disease is transmitted by the bite of an infected mosquito which has previously sucked the blood of a person suffering from malaria. The infected individual initially experiences chills for 15 to 60 minutes coincident with the release of a brood of merozoites. This is usually accompanied by headache, nausea, and vomiting, and is succeeded by chills and a febrile stage lasting several hours. The infections may be asymptomatic or may terminate in death. The parasitized red blood cells—especially in the case of falciparum malaria—become sticky and plug up the smaller vessels. The obstructing action has a variety of effects: tissue anoxia and necrosis, bursting of vessels, electrolyte imbalance, etc., affecting many organs.

Human leishmaniasis is caused by protozoal species and subspecies of the genus Leishmania. Nonhuman mammals (e.g., dogs, cats, rodents, horses, sheep, and cattle) are the reservoirs for this infection, which is transmitted to man most often by the bites of infected female sandflies. Four morphologically indistinguishable species infect humans: *L. donovani, L. tropica, L. mexicana,* and *L. braziliensis,* producing visceral leishmaniasis, cutaneous leishmaniasis, and mucocutaneous leishmaniasis. In the case of visceral leishmaniasis, the intracellular amastigote form multiplies chiefly in macrophages and produces a disease of various parts of the reticuloendothelial system, causing severe hepatosplenomegaly, along with enlargement of lymph nodes, fever, fatigue, malaise, and secondary infections, and usually is fatal if untreated. The most common clinical manifestations in cases of cutaneous and mucocutaneous leishmaniasis are characterized by formation of ulcers and lesions to the skin and mucous membranes.

Effective and practical antiparasitic vaccines have yet to be devised, and chemotherapy is thus the most efficient and inexpensive single method to control most parasitic infections. Safe and effective drugs are still needed to prevent or treat some major parasitic infections, for example, leishmaniasis, cryptosporidiosis, and malaria.

At present, notwithstanding the fact that more than hundreds of different compounds have been tested, no completely effective treatment for most protozoans in man or animals has been disclosed. Most attempts at conventional chemotherapy with known antiparasitic, antifungal, antibiotic or antiviral agents have been unsuccessful. Other pharmaceuticals, for example, the antimalarials (i.e., chloroquine phosphate, primaquine phosphate, and pyrimethamine sulfadoxine) are losing their utility because of the development of drug resistance. Of greatest concern is the spread of multidrug-resistant strains of *P. falciparum,* the most dangerous and prevalent plasmodial species. Pharmaceuticals such as amphotericin B and pentamidine isethionate, indicated for treatment of leishmaniasis, have proven unsatisfactory because they cause unacceptable levels of toxicity at therapeutic doses.

Several colostrum preparations have been used to treat some protozoal infections, such as *C. parvum,* the best results being obtained with hyperimmune bovine colostrum harvested from dairy cows vaccinated with *C. parvum* antigens. Treatment of protozoal gastrointestinal disorders of parasitic protozoan origin by administration of hyperimmune milk products is disclosed in U.S. Pat. No. 5,106,618 (Apr. 21, 1992) to Beck et al. Despite promising indications, considerable variation has been observed in the therapeutic efficacies of different colostrum preparations. As a result, current treatments center around palliative remedies in addition to treatment with antidiarrheal compounds and fluid and electrolyte replacement to alleviate the dehydration accompanying diarrheal illness.

None of these aforementioned references and publications, however, is believed to disclose or suggest the use of Syringomycin-family lipodepsipeptides as a method of/for controlling or preventing infections caused by protozoans. From the foregoing, it would be advantageous to provide methods for combating and preventing protozoal infections in mammals.

DISCLOSURE OF THE INVENTION

The present invention relates to a method of controlling or preventing infections caused by protozoans using syringomycin-family lipodepsipeptides. Preferably, the invention involves a method of treating or preventing infections caused by protozoans using syringomycin-E. Even more preferably, the present invention relates to a method of controlling *C. parvum, P. falciparum,* and *L. donovani* infections using a pharmaceutically effective amount of syringomycin-E.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 1 is a graph illustrating the inhibitory effect of Syr-E on *C. parvum* development, monitored in a BFTE cell culture at pH 6.3;

FIG. 2 is a graph illustrating the toxic effect of Syr-E at pH 6.3 using a neutral red assay;

BEST MODE OF THE INVENTION

Figure 3:
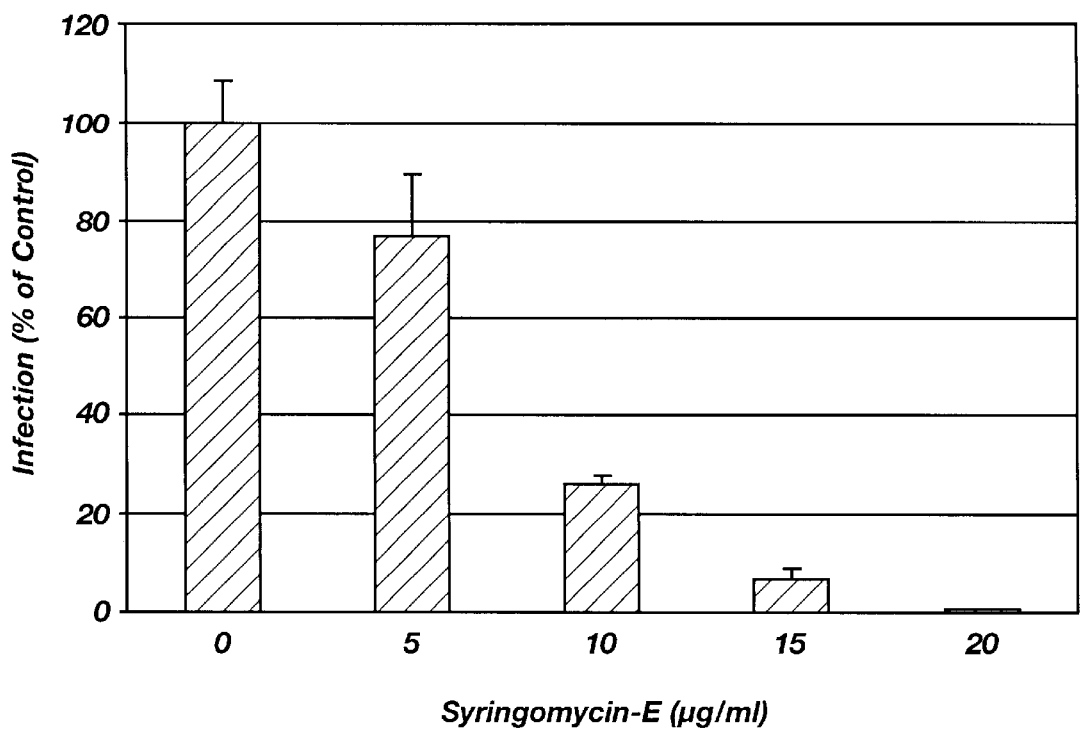
FIG. 3 is a graph illustrating the inhibitory effect of Syr-E on *C. parvum* development in MDBK cells.

The invention comprises administration of a syringomycin-family lipodepsipeptide compound (or compounds) ("SLPs") to control infections caused by a protozoan. Administration of SLPs disrupts the permeability of cell membranes. Although both amphotericin B and Syr-E cause ion channel formation in the plasma membrane, it is understood that the mechanism of action of these two agents differs. Amphotericin B binds ergosterol, while Syr-E requires both ergosterol and sphingolipids for channel formation. A clear indication of the different modes of action and membrane compositional requirements for each agent is evidenced by observed resistance of yeast mutants (defective in sphingolipid biosynthesis) to Syr-E, but not to Amphotericin B. As will be apparent from the hereinafter described Examples, SLPs administered as described herein cause a significant reduction in the infectivity of protozoans, including, for example, *C. parvum, P. falciparum,* and *L. donovani.*

The term "animal" is intended to mean, for the purpose of this invention, any living creature including mammals (e.g. humans, domestic animals, farm animals, and wild animals). The term "gastrointestinal disorder" as used herein means infections relating to the stomach, intestine, gall bladder, and/or biliary tract of a mammal that result in a disturbance of the same in terms of function, structure, or both.

The terms "treating" and "treatment" are intended to mean the amelioration or complete elimination of the symptoms of the disorder and/or the pathogenic origin of the disorder as part of therapeutic or prophylactic therapy. The term "administer" is intended to mean any method of treating a subject with a substance, such as orally, intravenously, intramuscularly, subcutaneously, topically, rectally, or via inhalation therapy.

SLPs are composed of a peptide moiety and a hydroxylated acyl chain. The core structure of some lipodepsipeptides is shown below:

As illustrated above, SLPs have nine amino acids. The carboxyl of the chlorothreonine is covalently bonded to the hydroxyl group of the N-terminal serine to form a macrocyclic ring.

The N-terminal serine is N-acylated by a long-chain unbranched acyl chain. The acyl chain is O-acylated by the C-terminal carboxyl of the acyl chain to form a macrolactone ring. It will be appreciated by one skilled in the art that the length of the acyl chain can vary without significantly altering the SLPs antiprotozoal activity. For example, in the core structure of SLP above, syringomycin-A1, syringomycin-E and syringomycin-G have n values of 6, 8 and 10, respectively.

The acyl chain is also hydroxylated, the hydroxy group being at the C-3 position of the acyl chain. However, it is understood that SLPs may have multiple hydroxyl groups without losing antiprotozoal activity.

The SLPs of the present invention can be used in the therapeutic and prophylactic treatment of protozoan infections in immunocompromised animals. The SLPs of the present invention are particularly useful to treat protozoan infections that occur in patients with human immunodeficiency virus, where current medical intervention is commonly limited to the palliative treatment of symptoms such as diarrhea, cramping abdominal pain, weight loss, nausea, vomiting, fatigue, headache, fever, malaise, formation of ulcers and lesions on skin and mucous membranes, secondary infections, and myalgia. Thus, prophylactic treatment of these immunocompromised patients can be used to avoid substantial morbidity. Patients undergoing immunosuppressive therapy and young children with insufficiently developed immune systems may likewise benefit from treatment with SLPs to prevent, control, or eradicate infections caused by protozoans. Further, SLPs may be used to treat immunocompetent subjects who are exposed to protozoans for the purpose of therapeutically treating or preventing the infection.

The SLPs of this invention may be used in conjunction with conventional anti-infective agents, antimicrobial agents, immunomodulators, protease inhibitors, and pharmaceutical preparations indicated for the treatment of symptoms associated with protozoal infections. It is believed that the aforementioned medicinal agents may interact synergistically with the lipodepsipeptides of this invention, particularly in the treatment of immunocompromised patients that may otherwise succumb to this opportunistic infection and its morbid consequences.

The SLPs to be administered according to the method of the present invention include, but are not limited to, bases and pharmaceutically acceptable salts (e.g. acid addition salts) thereof. Examples of pharmaceutically acceptable acid addition salts include salts of inorganic acids such as sulfuric, nitric, phosphoric, and hydrochloric acid, as well as organic acids such as acetic, propionic, succinic, fumaric, maleic, citric, tartaric, cinnamic, lactic, mandelic, and ethanedisulfonic acid. The salts may be made by reacting the free base of the particular SLPs with the chosen acid in a stoichiometric ratio in an appropriate solvent. The salts may $$H_3C-(CH_2)_n-CH(OH)-CH_2-[Ser]-Ser-Dab-Dab-Arg-[Phe-Asp(OH)-Thr(Cl)]$$

be used, for example, in the preparation of oral and injectable formulations containing protease inhibitors as an active ingredient.

Oral and injectable formulations to be used according to the method of the present invention may also be incorporated into a pharmaceutical dosage form in order to protect the SLPs from unwanted biodegradation processes or to create a sustained-release effect. Administration of pH-sensitive SLPs can be accomplished by employing several methods to reduce acid hydrolysis in the stomach. These methods include the use of enteric coating, microencapsulation, lipid encapsulation, or administration of a buffer agent (e.g., with antacids) prior to, or concomitantly with, the administration of a formulation containing the SLPs to protect the SLPs from acids and enzymes created in portions of the gastrointestinal tract.

In another form of this invention there is provided a method for the treatment of infections with protozoans, such as, for example, C. parvum, L. donovani, and P. falciparum, in a mammal which comprises administering to the mammal a therapeutically effective amount of syringomycin. In a preferred embodiment of the invention, a therapeutically effective amount of Syringomycin-E is administered to the mammal for the treatment or prevention of infections with protozoans.

The invention also includes a method of making pharmaceutical dosage forms containing a syringomycin-family lipodepsipeptide for use in treating or preventing protozoal infections.

Having now generally described the invention, the same will be further described by reference to certain specific examples which are provided herein for purposes of illustration only and which are not intended as limiting.

EXAMPLES

Example I (Preparation of SLP for Antiprotozoal Experiments)

Syringomycin-E ("Syr-E") was produced from cultures of Pseudomonas syringae pv. syringae strain B301D. Strain B301D was grown in potato dextrose broth as described by Zhang, L., and J. Y. Takemoto, Effects of Pseudomonas Syringae Phytotoxin, Syringomycin, On Plasma Membrane Functions of Rhodotorula Pilimanae. *Phytopathol.* 77(2):297–303 (1987). Syr-E was purified by high performance liquid chromatography as described previously by Bidwai, A. P., and J. Y. Takemoto, Bacterial Phytotoxin, Syringomycin, Induces a Protein Kinase-Mediated Phosphorylation of Red Beet Plasma Membrane Polypeptides, *Proc. Natl. Acad. Sci. USA.* 84:6755–6759 (1987).

Liquid RPMI 1640 (RPMI) medium with L-glutamine and without sodium bicarbonate (Sigma Chemical Co., R-6504; St. Louis, Mo.) buffered with 0.165M MOPS (34.54 g/liter) was used for in vitro antiprotozoal tests. The recommended pH for dissolving and using Syr-E is below 6.5. The effect of Syr-E on host cells and *C. parvum* development was tested at both pH 6.3 and 7.0. The medium was adjusted to pH 7.0 with 10M NaOH and filter sterilized. Due to a high toxic effect of the low pH to host cells, Syr-E used in medium at pH 7 was immediately diluted from a stock solution at pH 6.0 prior to application.

Example II (Preparation of C. parvum in Cell Culture)

*C. parvum* (bovine isolate) oocysts used in this study were originally donated by the U.S. Department of Agriculture, Ames, Iowa. The oocysts were isolated from calf manure, preserved in 2.5% potassium dichromate at 4° C., and used within 3 months of purification. Oocysts were decontaminated by suspension in 20% (vol/vol) 1.05% sodium hypochlorite on ice for 20 minutes. Oocysts were then washed three times in Hanks' balanced salt solution ("HBSS") and once in RPMI 1640 (available from Sigma, St. Louis, Mo.). Release of sporozoites was achieved by incubating oocysts in an excystation solution consisting of 0.25% (wt/vol) trypsin (available from Sigma, St. Louis, Mo.) and 0.75% (wt/vol) taurodeoxycholic acid (available from Sigma) in HBSS. The resulting suspension was incubated at 37° C. for 45 minutes and microscopically observed to confirm sporozoite release. Sporozoites were completely separated from intact oocysts and oocyst walls by passage through sterile polycarbonate filters (3 micron pore size, available from Millipore Corp., Bedford, Mass.) twice prior to inoculation of bovine fallopian tube epithelial ("BFTE") cell monolayers.

Primary BFTE cell cultures were prepared from bovine fallopian tubes (FT). Fat was trimmed from the serosal surfaces, mucus was gently squeezed from the lumens, and FT were decontaminated by being submerged in 70% ethanol for 30 seconds. The FT were then transferred to sterile culture petri dishes containing HBSS and washed twice. The BFTE cells were harvested either by flushing the FT with HBSS, using a 10 ml syringe equipped with a mouse feeding needle, or by opening the FT lengthwise with scissors and scraping the mucosal surfaces. The BFTE cells were subsequently washed in HBSS by centrifugation at 200×g (force of gravity) for 10 minutes, planted in 75-cm$^2$ flasks containing RPMI 1640 and cultured in a 5% $CO_2$ incubator at 37° C. for 72 to 120 hours. When the cell lines reached confluency, they were trypsinized, split, and planted onto cover slips positioned on the bottoms of individual wells in 24-well tissue culture plates. When cells reached 80% confluency, they were inoculated with either $10^5$ oocysts or $4\times10^5$ sporozoites per well. Plates were then maintained at 37° C. in a candle jar environment (17% $O_2$, 3% $CO_2$, 80% $N_2$). Growth medium was changed in each well every 72 hours. In wells inoculated with oocysts, the medium was first changed at 24 hours to remove any unexcysted oocysts.

Coverslips were removed at 5, 24, 48, 72, 96, and 120 hours from the inoculated wells containing monolayers of BFTE cells. The coverslips were washed in RPMI 1640, fixed in 100% methanol for 10 minutes, rinsed twice with 25 mM PBS, and stained with an indirect immunofluorescent assay (IFA) using monoclonal antibody (Mab) 5H11. Mab 5H11 specifically reacts with an antigen present on intermediate stages of *C. parvum* development. Coverslips were then mounted on glass slides and examined under oil immersion (1000×), using bright-field microscopy. Parasites were enumerated by counting all developmental stages of *C. parvum* present in a single scan (67 fields) through the center of each coverslip. The data were statistically compared for significance, using analysis of variance (Fischer's protected least-significant-difference test using a "STATVIEW" statistical analysis application developed by Abacus Concepts, Inc., Berkeley, Calif.).

Successful infections were observed in BFTE cells inoculated with both oocysts and purified sporozoites. Parasites developed at the microvillous surface of BFTE cells in an intracellular but extracytoplasmic location. Significantly, multiple infections were common in individual cells, similar to those frequently observed in vivo.

To confirm the production of infective oocysts in cell culture, an immunosuppressed mouse model for cryptosporidiosis was used. Three groups of adult female C57BL/6N mice (6 weeks of age, each weighing 14 to 16 grams, purchased from Taconic, Germantown, N.Y.) were immunosuppressed with dexamethasone phosphate (available from Sigma, St. Louis, Mo.) provided in drinking water at a dosage level of 12 $\mu$g/ml. At 120 hours post-inoculation, coverslips from individual 24-well plates were collected, and the surfaces were scraped and pooled for each plate. All mice in a group were gavaged on day 7 immunosuppression with an equal volume of the resulting cells, cell products, and parasites (plate product) harvested from a single plate. Group 1 (four mice) and group 2 (five mice) received the plate product from plates inoculated with oocysts and sporozoites, respectively. Group 3 (five mice) was treated the same as group 1 except that the plate product was first suspended in 70% ethanol for 10 minutes to kill all stages of C. parvum except the oocysts. Fecal samples were collected from recta each day from mice in all groups and monitored for oocyst shedding, using oocyst-specific monoclonal antibody-based indirect immunofluorescence assay. Oocysts produced in BFTE cell culture were infective for immunosuppressed adult female mice. Also tested were two additional groups infected with non-cell culture derived oocysts. For further details on the complete experiment, see Yang et al., Infection and Immunity 64:349–354 (January 1996), the contents of which are incorporated herein by this reference.

Madin-Darby bovine kidney (MDBK) epithelial cells were also used to culture C. parvum in this study. Dulbecco's modified Eagle medium (DMEM) with 10% FBS was used for routine passage of MDBK cells purchased from American Type Collection for Culture (Rockville, Md.). Mycoplasma contamination was periodically checked with Hoechst staining (Uphoff et al., 1992). At confluence, MDBK cells were lifted from culture flasks with trypsin, enumerated, and redistributed to assay plates. Ninety-six well cell culture plates were employed to assess cytotoxicity of testing agents or the parasite or both to host cells using neutral red staining or lactic dehydrogenase (LDH) assay.

Neutral red assay was used to measure viewable cell damage, such as obvious plaque forming and cell peeling. Briefly, 0.1 ml of neutral red was directly added to supernatant in each well of 96-well plates at the termination of the culture. Following 1-hr incubation at 37°C., the supernatant mixture from each well was discarded and cells at the bottom of the wells were rinsed twice with PBS. A volume of 0.2 ml/well extract buffer was added and the content in each well was well mixed prior to 30 min. incubation in the dark at 25°C. cytotoxicity was quantitatively read using a Microplate Autoreader (Bio-Tek Instruments, Inc., Winooski, Vt.) with a wavelength set at 540 nm.

Lactic dehydrogenase assay was used to detect mild cytotoxicity which showed no discernable difference from naked eye observation. A volume of 10 $\mu$l/well culture supernatant was pipetted into a 96-well plate and mixed with 50 $\mu$l/well substrate solution containing 0.75 mM sodium pyruvate and 1 mg beta-NADH/ml. Following incubation at 37° C. for 30 min, the plate was added with 50 $\mu$l of 2,4-dinitrophenylhydrazine/well and kept at 25° C. for 20 min., and then the plate was added with a volume of 200 $\mu$l/well of 0.6 N NaOH, mixed well, and retained at 25° C. for 10 min. prior to being quantified by the Microplate Autoreader with a wavelength set at 515 nm.

For enumeration of C. parvum development in culture, 24-well plates were used with a sterile glass coverslip placed in each well. DMEM base was used at and post C. parvum inoculation.

Example III (Preparation of L. donovani in Cell Culture)

L. donovani parasites (WHO designation: MHOM/SD/62/1S-CL2D) used in this study were originally donated by the National Institutes of Health. These parasites were maintained as axenic amastigote-like forms by serial passage at 37°C. in a humid atmosphere containing 5% $CO_2$ using a slightly modified version of the medium described by Joshi et al., Cloning and characterization of differentially expressed genes from in vitro-grown 'amastigotes' of Leishmania donovani. *Molecular and Biochemical Parasitology*, 1993. 58: p. 345–354, the contents of which are incorporated herein by this reference.

*L. donovani* amastigote-like forms were seeded at 106 cells/ml in 96-well flat-bottom plates (Costar) in the amastigote medium described above in the presence or absence of drugs. The final volume in each well was 60 μl. Wells containing control parasites included 1% DMSO, the maximum concentration of the vehicle found in drug-containing samples. Plates were incubated at 37° C. in a humid 5% $CO_2$ atmosphere for 72 hours, then 12 μl of the aqueous CellTiter solution (Promega) was added to each well according to the instructions of the manufacturer. Plates were returned to the 37° C. incubator for a further 4–5 hours, then the absorbance of each well was measured at 490 nm using a SpectraMax Plus plate reader (Molecular Devices, Sunnyvale, Calif.). $IC_{50}$ values for each of the drugs (the concentration of drug that inhibited the growth of parasites by 50% compared to controls) was determined with the aid of the program SoftMax Pro (Molecular Devices). The log dose response equation $y=((a-d)/(1+(x/c)^b))+d$ was used to calculate $IC_{50}$ values, where x=drug concentration, y=absorbance at 490 nm, a=upper asymptote, b=slope, $c=IC_{50}$, and d=lower asymptote.

Example IV (Preparation of *P. falciparum* in Cell Culture)

*P. falciparum* used in this study were two well characterized clones, W2 and D6, as described in Oduola, A. M. et al., Plasmodium falciparum: cloning by single-erythrocyte micromanipulation and heterogeneity in vitro; *Exp. Parasitol.* 66, 86–95 (1988), the contents of which are incorporated herein by this reference. W2 is a clone of the Indochina I isolate and is resistant to chloroquine and pyrimethamine, but susceptible to mefloquine. D6 is a clone from the Sierra I/UNC isolate and is susceptible to chloroquine and pyrimethamine, but has reduced susceptibilities to mefloquine and halofantrine. Both of these clones have demonstrated susceptibility to artemisinin derivatives, with D6 usually having a 2–4 fold higher $IC_{50}$ for any particular artemisinin derivative.

Example V (Effect of Syringomycin on *C. parvum*)

To study the effect of host cell treatment with Syr-E on *C. parvum* infection, an experiment was designed as listed in Table 1. A single concentration of Syr-E at 15 μg/ml was used to treat MDBK cells at pH 7 with *C. parvum* infection. Group 1 served as an infection control, receiving no Syr-E treatment. Syr-E was administered 1 day prior to parasite inoculation to groups 2, 4, and 5, at the inoculation day to groups 3–5, and 1 day post inoculation to groups 3 and 5, respectively. Following specified administration day(s), supernatants of corresponding wells containing Syr-E were removed and replaced with fresh DMEM base. Cytotoxicity was monitored using lactic dehydrogenase (LDH) assay on day 1 post inoculation. Three coverslips from each group were collected on days 2 and 5 post inoculation, were fixed, and were stained with the specific IFA, as described with reference to Example II.

A pilot study demonstrated that MDBK cells were more resistant to Syr-E-related cytotoxicity than primary BFTE cells and Syr-E at neutral pH was able to reduce C. parvum development. Therefore, MDBK cells were employed to explore the inhibitory effect of Syr-E on C. parvum development in vitro, as shown in FIG. 3. Syr-E at 5.0 µg/ml significantly (P<0.05) reduced the infection percentage on day 2 post inoculation when compared to the untreated control. Data, collected on day 2 post inoculation, was transferred to percentage infection using the untreated group (0) as 100% and presented as the means +/− standard error of the mean. A dose-responding curve showed more inhibition on C. parvum development as the Syr-E concentration increased. At the highest concentration (20 µg/ml) used, Syr-E inhibited the parasite growth and development by 99.5%. Statistically, post-hoc comparisons between groups achieved significant (at least P<0.05) levels except two groups with Syr-E at 15 and 20 µg/ml, respectively. Furthermore, observation on the untreated control and Syr-E 15 µg/ml was extended to day 5 post inoculation, and the infection percentage in the Syr-E treated group was only 14.7% (±2%) of the untreated control.

Figure 4:
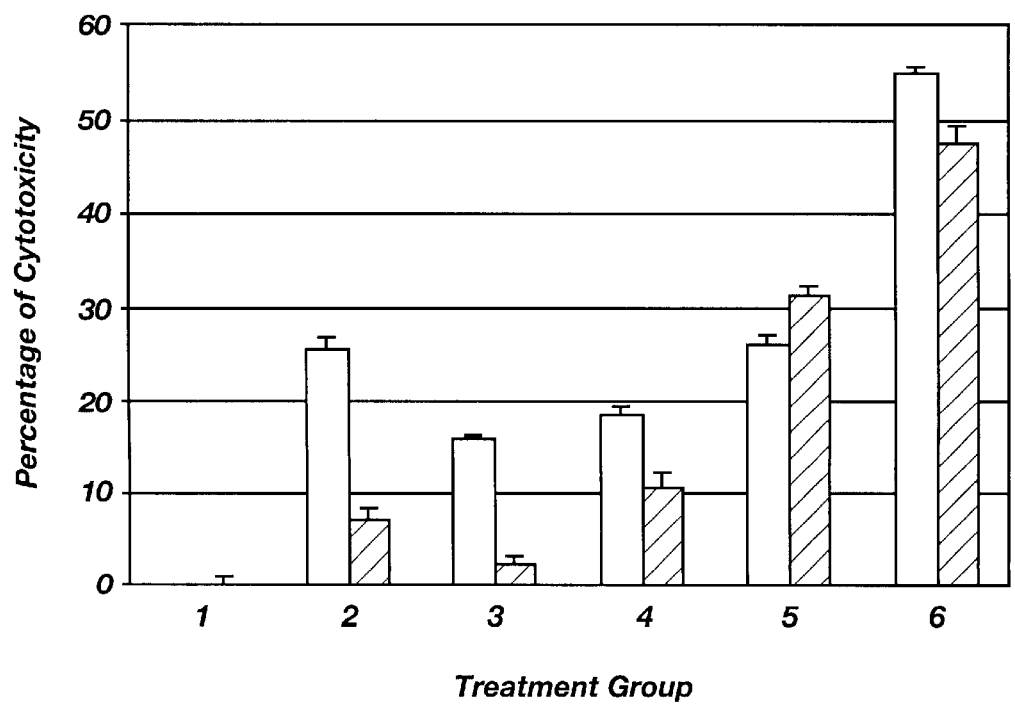
FIG. 4 is a graph illustrating cytotoxicity of Syr-E to host cells, measured using a lactic dehydrogenase assay.

As illustrated in FIG. 4, samples were collected on days 1 (empty bar) and 2 (solid bar) post inoculation and analyzed using a LDH assay. Group 1 received neither Syr-E treatment nor inoculation and its cytotoxicity was set at 0%, as illustrated on day 2. Group 2 received only C. parvum inoculation serving as an infection control. Groups 3–6 received both the inoculation and Syr-E treatments at 5, 10, 15, and 20 µg/ml, respectively. Data in FIG. 4 are presented as the means +/− standard errors of the mean. No obvious cell peeling or plaques formed on cell monolayers. Cytotoxicity of Syr-E to host cells was measured using LDH assay on both days 1 and 2 post inoculation. More (P<0.01) cytotoxicity was shown on day 1 post inoculation than day 2 post inoculation. At pH 7.0, Syr-E related cytotoxicity appeared at 20 µg/ml on day 1 post inoculation, and 15 and 20 µg/ml on day 2 post inoculation when compared to the infected and untreated control (group 2). Overall, more cytotoxicity was observed as Syr-E concentrations increased.

As shown in Table 1, all Syr-E treatment groups significantly (P<0.001) reduced C. parvum infection in MDBK cell culture at pH 7. A single day treatment prior to the inoculation reduced the parasite infection to 13% and 22% on days 2 and 5 post inoculation, respectively. An additional treatment day at the inoculation further significantly (P<0.05) decreased the infection percentage to approximately 1%. This reduction trend of the infection percentage was not significantly extended when one more day of Syr-E treatment was added on Day 1 post inoculation. Comparison of groups with 2 day Syr-E treatment (Groups 3 and 4) revealed that the infection percentages were significantly (P=0.077 and P=0.061) lower in Group 4 than in Group 3 on both days 2 and 5 post inoculation. Statistical analysis demonstrated no significant changes of the infection percentages between days 2 and 5 post inoculation within individual groups. There was no visual cell damage observed in this experiment and monitoring cytotoxicity with a LDH assay on day 1 post inoculation failed to show significant differences between groups except group 3 which had a significantly (P<0.01) lower LDH reading than the untreated control.

TABLE 1

Schedule of Syr-E treatments and the effect on C. parvum infection in MDBK cells

| Group | Syr-E Treatment Days and Time | Infection % (Day 2)* | Infection % (Day 5) |
|---|---|---|---|
| 1 | No Syr-E, served as infection controls | 100.0 ± 6.4 | 100.0 ± 5.4 |
| 2 | 1 day, prior to inoculation | 12.9 ± 2.7$^A$ | 21.9 ± 5.3$^A$ |
| 3 | 2 days, at and post inoculation | 10.2 ± 2.1$^A$ | 11.7 ± 1.6$^A$ |
| 4 | 2 days, prior to and at inoculation | 1.1 ± 0.2$^{ABC}$ | 1.4 ± 0.5$^{ABC}$ |
| 5 | 3 days, prior to, at, and post inoculation | 0.9 ± 0.1$^{ABC}$ | 1.0 ± 0.3$^{ABC}$ |

Notes: *Samples were collected on Days 2 and 5 post inoculation. Results were expressed as infection percentage of the untreated control (Group 1), using the means ± standard errors of the mean.

A, at least P<0.001 when compared to Group 1; B, at least P<0.05 when compared to Group 2; and C, at least P<0.08 when compared to Group 3.

Example VI (Inhibition of C. parvum infection at pH 6.3)

Figures 1, 2:
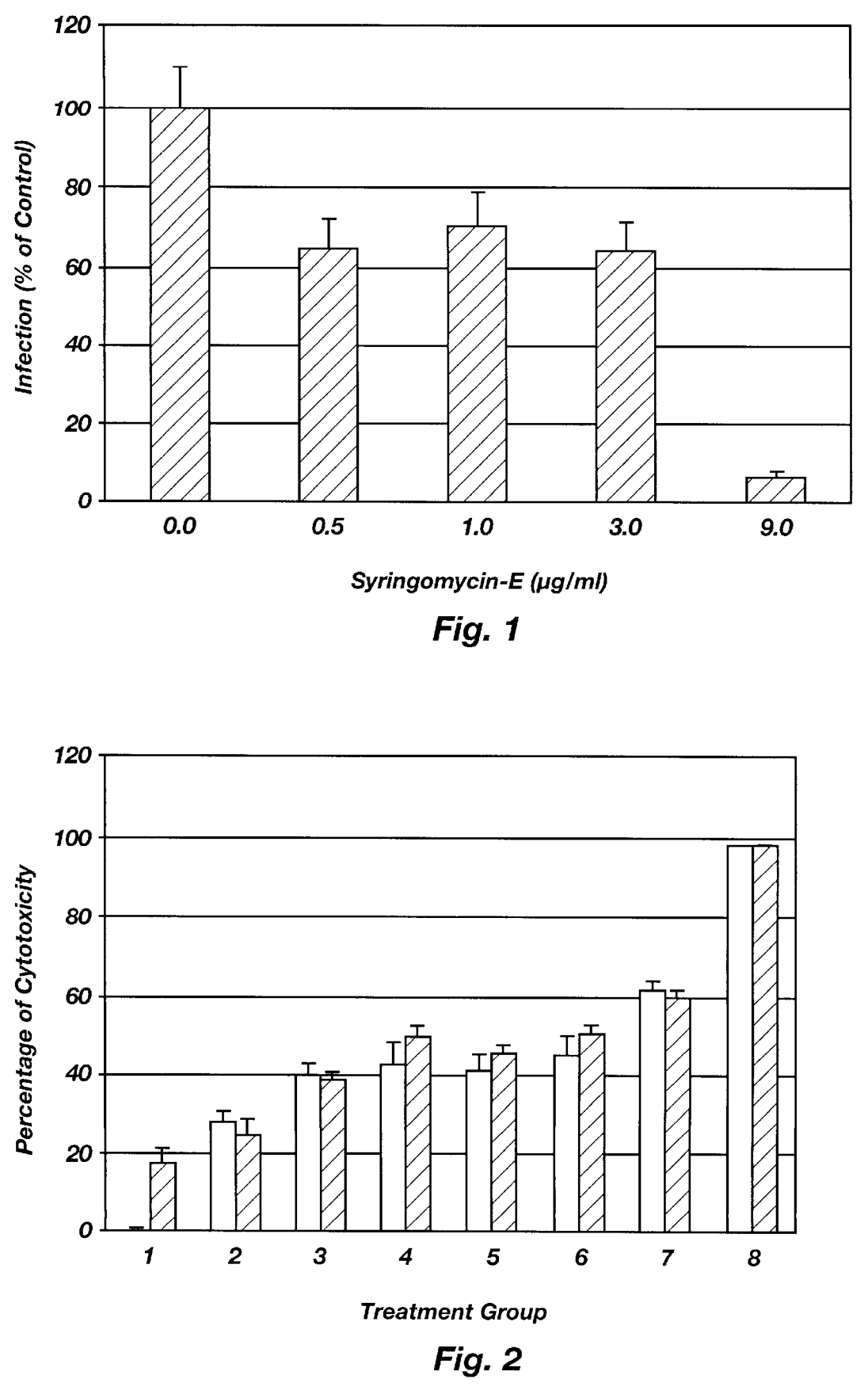

The inhibitory effect of Syr-E on C. parvum development was monitored in BFTE cell culture at pH 6.3. All four concentrations (0.5, 1.0, 3.0, and 9.0 µg/ml) of Syr-E significantly (at least P<0.01) reduced the infection percentage more than non-treated controls, as shown in FIG. 1. The parasite numbers in Syr-E treatments from 0.5 to 3.0 µg/ml did not vary significantly, however, an increase of Syr-E to 9.0 µg/ml further reduced the infection percentage significantly (P<0.01). Visual cell plaques were observed in this experiment. Data, collected at day 2 post inoculation, was transferred to percentage infection using the untreated group (0.0) as 100% and presented as the means +/− standard error of the mean.

A separate experiment to measure the toxic effect of Syr-E at pH 6.3 using the neutral red assay (FIG. 2) revealed that such low pH itself caused 28% cytotoxicity (see group 2) to host cells. Samples were collected on day 2 post inoculation. Each group consisted of both uninfected (empty bar) and C. parvum infected (solid bar) subgroups. In group 1, the medium pH was adjusted to 7.2, no Syr-E was used, and the cytotoxicity of the uninfected subgroup set to zero percent. Medium pH in groups 2–8 was adjusted to 6.3 and groups 3–8 received Syr-E treatments at 1, 2, 4, 8, 16, and 32 ,g/ml, respectively. Data are presented as the means +/− standard error of the mean. The cytotoxic effect increased from approximately 40% to 60% as Syr-E concentrations were elevated from 1 to 16 µg/ml, presenting a dose-dependent response. Such cytotoxicity was significantly (P<0.05) enhanced by the presence of C. parvum infection. BFTE cells were 98% destroyed when Syr-E concentration reached 32 µg/ml at pH 6.3.

Example VII (Effect of Syringomycin on P. falciparum)

The susceptibility of P. falciparum to Syr-E was studied using a modified antimalarial drug susceptibility screen following the procedures published by Desjardins et al., Quantitative assessment of antimalarial activity in vitro by semiautomated microdilution technique (1979), with modifications developed by Milhous et al., In vitro strategies for circumventing antimalarial drug resistance, Prog. Clin. Biol.

Res. 313:61–72 (1980), the contents of which are incorporated herein by this reference. Generally, the assay relied on the incorporation of radiolabeled hypoxanthine by the parasites, with inhibition of isotope incorporation being attributed to activity of known or candidate antimalarial drugs. For each assay, proven antimalarials, such as chloroquine, mefloquine, quinine, artemisinin, pyrimethamine and sulfadoxine, were used as controls. The incubation period was 66 hours and the starting parasitemia was 0.2%, with a 1% hematocrit. RPMI-1640 culture media with no folate or p-aminobenzoic acid (PABA) was used as the media.

Syr-E was dissolved directly in dimethylsulfoxide (DMSO) and diluted 400 fold with complete culture media and started at a highest concentration of 50,000 ng/ml. The Syr-E was then diluted 2-fold, 11 times, to give a concentration range of 1,048 fold. These dilutions were performed automatically by a Biomek 1000 or 2000 Liquid Handling System into 96-well microtiter plates. The diluted drugs were then transferred (25 $\mu$l) to test plates, and 200 $\mu$l of parasitized erythrocytes (0.2% parasitemia and 1% hematocrit) were added and incubated at 37° C. in a controlled environment of 5% $CO_2$, 5% $O_2$ and 90% $N_2$. After 42 hours, 25 $\mu$l of $^3$H-hypoxanthine was added and the plates incubated for an additional 24 hours. At the end of the 66 hour incubation period, the plates were frozen at –70° C. to lyse the red cells and later thawed and harvested onto glass fiber filter mats by using a 96-well cell harvester. The filter mats were then counted in a scintillation counter and the data downloaded with custom, automated analysis software (developed at the Walter Reed Army Institute of Research). For each drug, the concentration response profile was determined and 50% inhibitory concentrations ($IC_{50}$) and 90% inhibitory concentrations ($IC_{90}$) were determined by using a nonlinear, logistic dose response analysis program.

Syr-E evaluations were performed at pH 7.0 with minimal delay between the addition of Syr-E and parasite inoculation for the purpose of providing as much exposure of the W2 and D6 isolates to Syr-E as possible and reducing possible loss of Syr-E efficacy. $IC_{50}$ values of 3.23 μg/ml and 3.03 μg/ml were determined for W2 and D6 isolates, respectively.

Example VIII (Effect of Syringomycin on *L. donovani*)

Activity of Syr-E against *L. donovani* was determined using a cell-free amastigote culture technique that included the uptake of a vital dye (Cell Titer solution, Promega Corporation) as a measure of parasite viability at 72 hours post inoculation. OD values for serial dilutions of Syr-E were transformed as described for the malaria screen (Example VII) to determine $IC_{50}$ values against Leishmania. The amastigote assay was performed at a pH of 5.5, which is favorable for Syr-E activity. As shown in Table 2, Syr-E had an $IC_{50}$ value of 0.101 μg/ml (101.15 ng/ml) against *L. donovani* challenge.

| Sample | Concentration | OD Values |
|---|---|---|
| 1 | 4.00000 | 0.099 |
| 2 | 2.00000 | 0.097 |
| 3 | 1.00000 | 0.090 |
| 4 | 0.50000 | 0.089 |
| 5 | 0.25000 | 0.090 |
| 6 | 0.12500 | 0.102 |
| 7 | 0.06250 | 0.678 |
| 8 | 0.03125 | 0.664 |
| 9 | 0.01563 | 0.709 |
| 10 | 0.00781 | 0.652 |
| 11 | 0.00391 | 0.672 |

Although the invention has been described in detail with respect to use of specific Syringomycin-family lipodepsipeptides and methods of treating infections caused by protozoal agents, it should be realized that certain modifications can be made within the scope and spirit of the invention by those skilled in the art.

What is claimed is:

1. A method of treating a protozoal infection in a mammal which comprises administering to said mammal a syringomycin lipodepsipeptide in an amount sufficient to interfere with the protozoal infection.

2. The method of claim 1 wherein said mammal is immunocompromised.

3. The method of claim 1 wherein said mammal is a human.

4. The method of claim 3 wherein said human has been infected with a human immunodeficiency virus.

5. The method of claim 1 wherein said syringomycin lipodepsipeptide comprises Syringomycin-E.

6. The method of claim 1 wherein said syringomycin lipodepsipeptide comprises Syringomycin-A.

7. The method of claim 1 wherein said syringomycin lipodepsipeptide comprises Syringomycin-G.

8. The method of claim 1 wherein the said syringomycin lipodepsipeptide is isolated from a plant bacterium *Pseudomonas syringae* pv. *syringae.*

9. The method of claim 1 wherein said protozoal infection is caused by *Plasmodium falciparum.*

10. The method of claim 1 wherein said protozoal infection is caused by *Leishmania donovani.*

11. The method of claim 1 wherein said protozoal infection is caused by *Cryptosporidium parvum.*

12. The method of claim 1 wherein said syringomycin lipodepsipeptide is administered to said mammal parenterally.

13. The method of claim 1 wherein said syringomycin lipodepsipeptide is administered to said mammal by parenteral route in microencapsulated form.

14. The method of claim 1 wherein said syringomycin lipodepsipeptide is administered to said mammal orally.

15. The method of claim 1 further comprising reapplying said syringomycin lipodepsipeptide in a sufficient amount to continue treatment of the protozoal infection and prevent reinfection.

16. A method of preventing a protozoal infection in a mammal which comprises administering to said mammal a syringomycin lipodepsipeptide in an amount sufficient to prevent the protozoal infection in said mammal.

* * * * *

UNITED STATES PATENT AND TRADEMARK OFFICE
CERTIFICATE OF CORRECTION

PATENT NO.     : 6,310,037 B1
DATED          : October 30, 2001
INVENTOR(S)    : Jon Y. Takemoto et al.

It is certified that error appears in the above-identified patent and that said Letters Patent is hereby corrected as shown below:

Column 3,
Line 63, change "H3C—(CH2)n—CH(OH)—CH2" to -- $H_3C$—$(CH_2)n$—CH(OH)—$CH_2$ --

Signed and Sealed this

Twenty-ninth Day of July, 2003

JAMES E. ROGAN
*Director of the United States Patent and Trademark Office*